(12) United States Patent
Raj et al.

(10) Patent No.: US 9,174,004 B2
(45) Date of Patent: Nov. 3, 2015

(54) PEN NEEDLE ASSEMBLY OUTER COVER HAVING A BREAKAWAY FLANGE

(75) Inventors: Abhijitsinh S. Raj, Parsippany, NJ (US); Joshua David Horvath, Sparta, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 12/205,699

(22) Filed: Sep. 5, 2008

(65) Prior Publication Data

US 2009/0069752 A1    Mar. 12, 2009

Related U.S. Application Data

(60) Provisional application No. 60/935,956, filed on Sep. 7, 2007.

(51) Int. Cl.
*A61M 5/32* (2006.01)

(52) U.S. Cl.
CPC ........... *A61M 5/3202* (2013.01); *A61M 5/3213* (2013.01)

(58) Field of Classification Search
CPC ............. A61M 2005/5073; A61M 2005/3279; A61M 5/5013; A61M 2005/325; A61M 2205/583; A61M 5/50; A61M 2005/312; A61M 5/3202; A61M 5/3213
USPC ......... 604/533, 534, 535, 536, 263, 192, 197, 604/198; 600/121; 283/81
See application file for complete search history.

(56) References Cited

U.S. PATENT DOCUMENTS

| | | | |
|---|---|---|---|
| 4,561,553 A * | 12/1985 | Crisci | 215/256 |
| 4,976,699 A * | 12/1990 | Gold | 604/192 |
| 2003/0047937 A1* | 3/2003 | Chaduc et al. | 283/81 |
| 2006/0032769 A1* | 2/2006 | Erickson et al. | 206/365 |
| 2006/0229562 A1* | 10/2006 | Marsh et al. | 604/164.01 |
| 2007/0149924 A1* | 6/2007 | Marsh | 604/117 |
| 2008/0183140 A1* | 7/2008 | Paproski et al. | 604/232 |

FOREIGN PATENT DOCUMENTS

| | | | |
|---|---|---|---|
| EP | 0 903 157 | 3/1999 | |
| EP | 1 138 338 | 10/2001 | |
| EP | 1138338 A1 * | 10/2001 | |
| JP | 60-36846 | 3/1985 | |
| JP | 63-281610 | 11/1988 | |
| JP | 9-509087 | 9/1997 | |
| JP | 11-137687 | 5/1999 | |
| JP | 2000271219 * | 3/2000 | A61N 5/32 |
| JP | 2000-271219 | 10/2000 | |
| JP | 2001-286562 | 10/2001 | |
| WO | WO 95/23005 | 8/1995 | |

* cited by examiner

*Primary Examiner* — Bhisma Mehta
*Assistant Examiner* — Brandy S Lee
(74) *Attorney, Agent, or Firm* — Dickinson Wright PLLC (57) ABSTRACT

An outer needle cover for a pen needle assembly is provided with a breakaway flange. Prior to use, the flange is connected to a body of the outer cover. The flange has a reduced cross sectional thickness portion that facilitates separation of the flange from the outer cover, thereby reducing the outer diameter of the outer cover. The reduced outer diameter of the outer cover allows the outer cover to be received by a pen cap of an existing injector device.

20 Claims, 9 Drawing Sheets

FIG. 11

PEN NEEDLE ASSEMBLY OUTER COVER HAVING A BREAKAWAY FLANGE

CROSS REFERENCE TO RELATED APPLICATION

This application claims the benefit under 35 U.S.C. §119(e) of provisional application Ser. No. 60/935,956, filed Sep. 7, 2007, which is hereby incorporated by reference in its entirety.

FIELD OF THE INVENTION

The present invention relates generally to an outer cover for a pen needle assembly. More particularly, the present invention generally relates to an outer cover having a breakaway flange, thereby allowing the outer cover to be received by a pen cap of a pen needle assembly.

BACKGROUND OF THE INVENTION

Insulin and other injectable medications are commonly given with drug delivery pens, whereby a disposable pen needle is attached to facilitate drug container access and allow fluid egress from the container through the needle into the patient.

As technology and competition advance, driving the desire for shorter, thinner, less painful, and more efficacious injections, the design of the pen needle and parts thereof becomes more and more important. Designs need to proactively address ergonomically improving injection technique, injection depth control and accuracy, the ability to be safely used and transported to disposal, and protection against misuse while maintaining the ability to be economically manufactured on a mass production scale.

Figure 1:
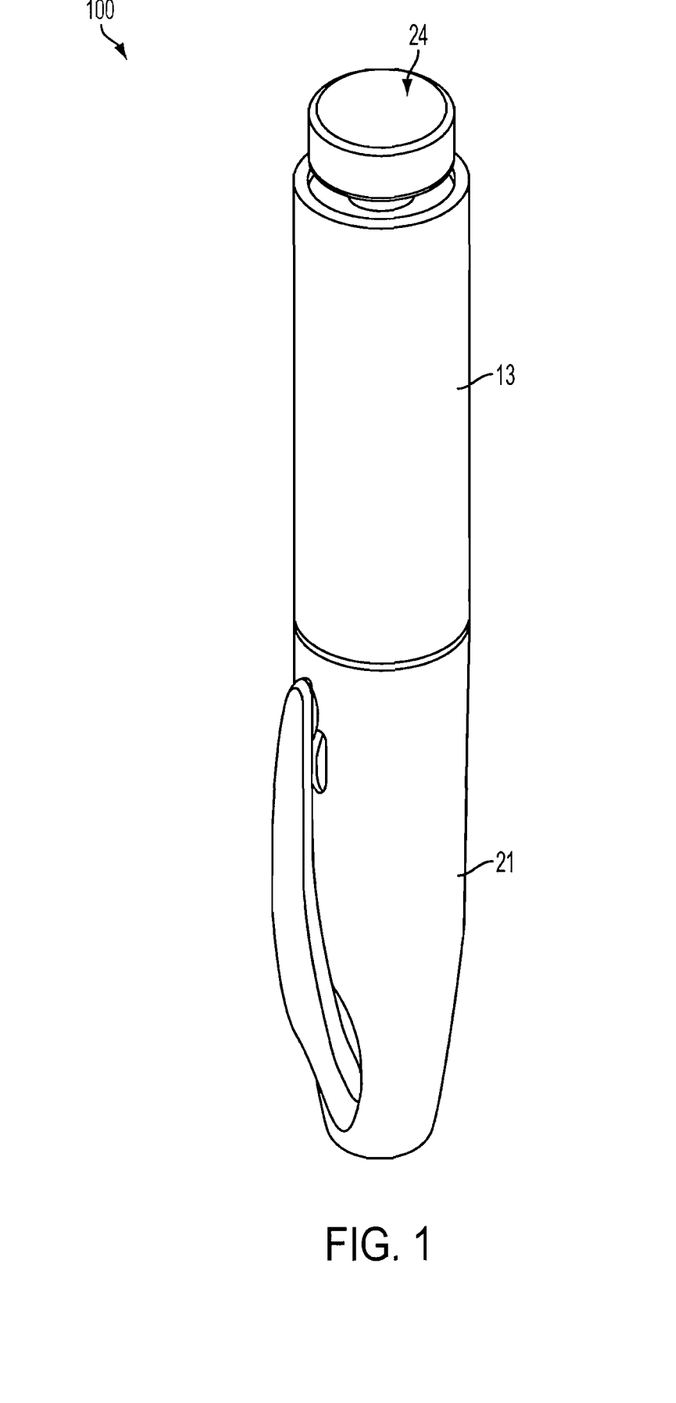
FIG. 1 is a perspective view of an assembled existing drug delivery pen.
Figure 2:
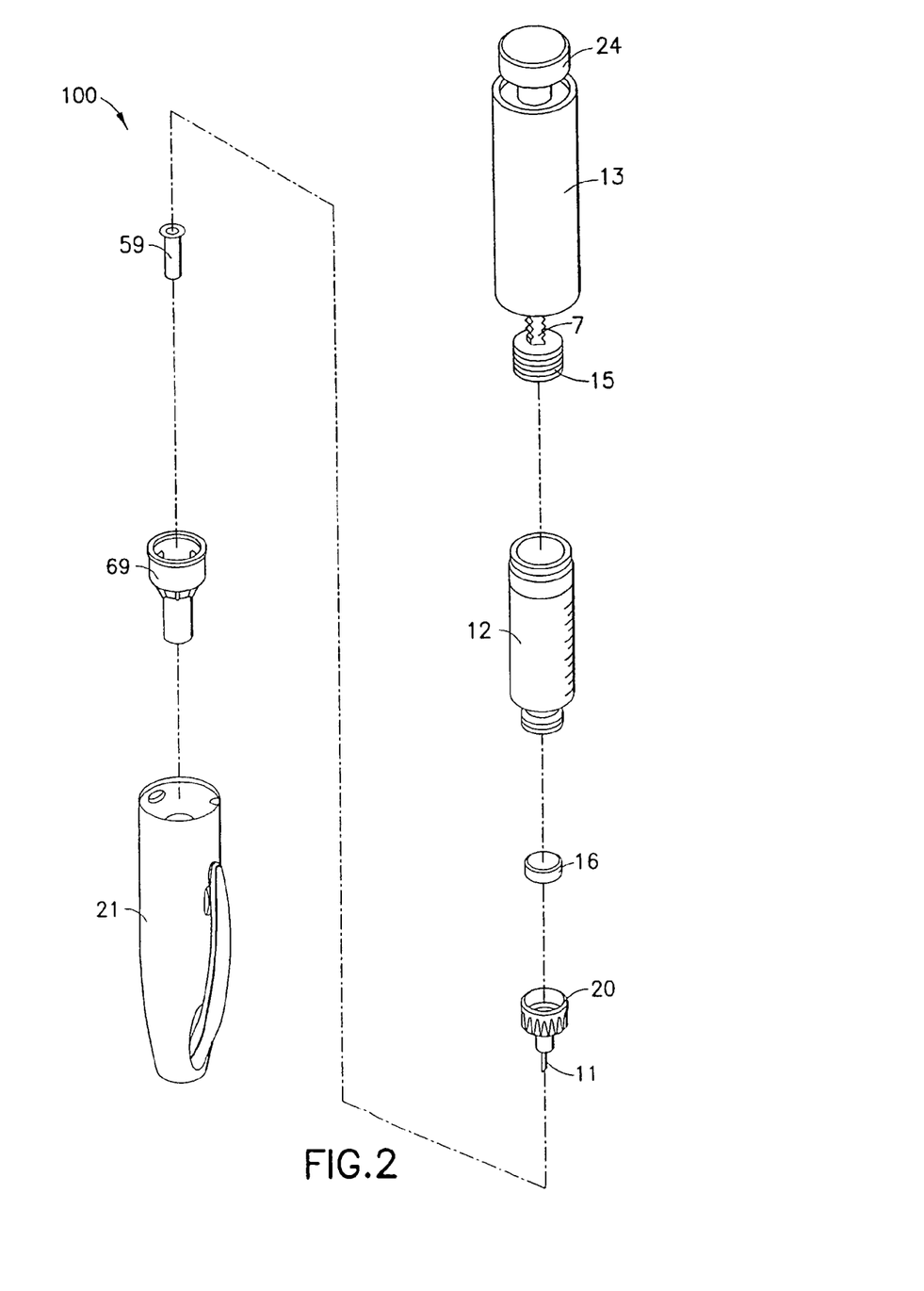
FIG. 2 is an exploded perspective view of the components of the drug delivery pen of FIG. 1.

Drug delivery pens, such as the existing drug delivery pen 100 shown in FIGS. 1 and 2, typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is used by the user to securely hold the pen injector device 100 in a shirt pocket, purse or other suitable location and provide cover/protection from accidental needle injury.

FIG. 2 is an exploded view of the pen needle assembly 100 of FIG. 1. The dose knob/button 24 has a dual purpose and is used both to set the dosage of the medication to be injected and to inject the dosed medicament via the lead screw 7 and stopper 15 through the medicament cartridge 12 attached through the reservoir housing or hub 20. In standard drug delivery pens the dosing and delivery mechanisms are all found within the outer sleeve 13 and are not described in greater detail here as they are understood by those knowledgeable of the prior art. The medicament cartridge 12 is typically attached to a standard pen injector housing via known attachment means, such as ¼ turn fastening features. The distal movement of the plunger or stopper 15 within the medicament cartridge 12 causes medication to be forced into the reservoir housing 20. The medicament cartridge 12 is sealed by septum 16, which is punctured by a septum penetrating needle cannula (not shown) located within hub 20. The hub 20 is preferably screwed onto the medicament cartridge 12, although other attachment means can be used. To protect the patient needle 11, an outer shield 69 attaches to the hub 20. An inner shield 59 covers the patient needle 11 within the outer shield 69. The cap 21 fits snugly against outer sleeve 13 to allow a user to securely carry the drug delivery pen 100.

Figure 3:
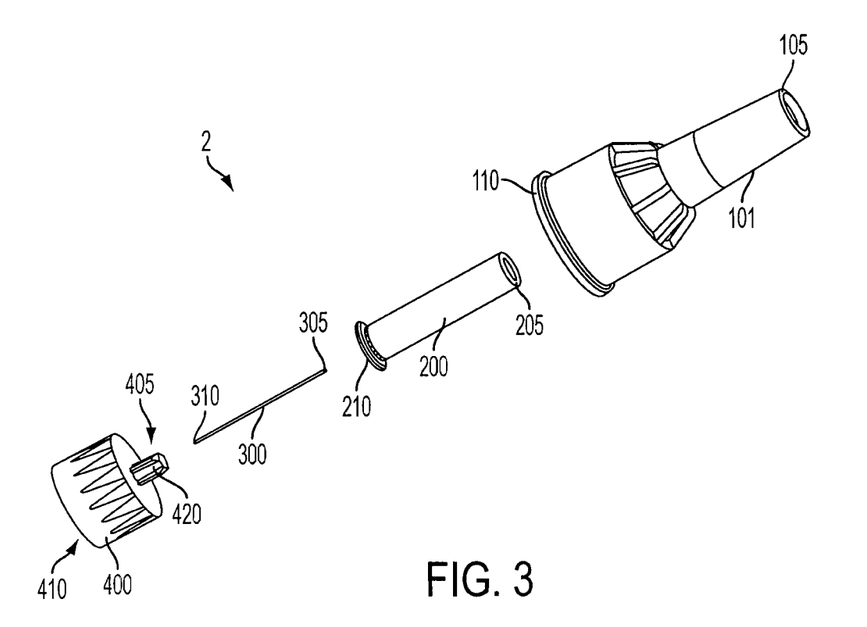
FIG. 3 is an exploded perspective view of a needle assembly for a drug delivery pen.

A pen needle assembly 2 is shown in FIG. 3 that is substantially identical to the pen needle assembly of FIG. 2. The needle assembly 2 includes a cover 101, an inner shield 200, a needle cannula 300, and a needle hub 400. A proximal end 310 of the needle cannula 300 is inserted into a center opening in the distal (patient) end 405 of the needle hub 400 until a predetermined length of the distal end 305 of the needle cannula 300 remains extended. The needle cannula 300 is secured by epoxy or adhesive in the distal end 405 of the hub 400 within the hub protrusion 420.

To protect users from injury and the needle cannula 300 from being damaged, the inner shield 200 covers the exposed portion of needle cannula 300. The open proximal end 210 of the inner shield 200 is placed over the exposed portion of needle cannula 300. The open proximal end 110 of the cover 100 envelops the inner shield 200, needle cannula 300, and hub 400.

Distal end 105 of the cover 101 is closed to prevent contamination and damage to the inner components of pen needle assembly 2, and to prevent injury to anyone who may handle it prior to use. The proximal end 410 of the hub 400 is typically covered by a sanitary cover (not shown) on end 110 of cover 101. The pen needle assembly 2 is then ready for shipment to a user. When the user is ready to use the pen needle assembly 2, the sanitary cover (not shown) is removed, the hub 400 is screwed onto a standard medication cartridge 12 (FIG. 2), and the cover 101 and inner shield 200 are separately removed from the hub 400/cannula 300 subassembly by a pulling action. The distal end 205 of the inner shield 200 is closed to cover the distal end 305 of the needle cannula 300 after the cover 101 is removed to protect the user from an accidental stick. The inner shield 200 is then removed to access the needle cannula 300. Thus, two separate pulling actions are required to remove both the cover 101 and the inner shield 200.

Figure 4:
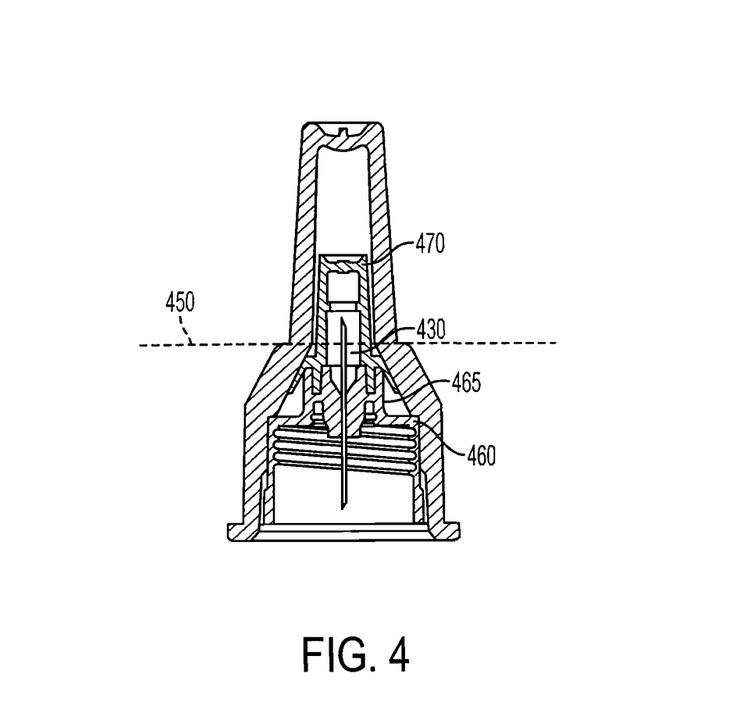
FIG. 4 is a cross-sectional view of a pen needle hub assembly in an as-manufactured state.

FIG. 4 is a cross-sectional view of a pen needle assembly in the configuration that it would be received by a user (with a sanitary cover not shown). An inner shield 470 covers a needle cannula 430. Additionally, the hub 460 includes a center hub protrusion 465. The skin contact plane 450 is the plane of the straight surface across the distal end of the center hub protrusion 465.

Many existing replacement needle assemblies include an inner shield 200 and an outer cover 101 as shown. The outer cover 101 typically has a cylindrical body and a thin, protruding flange 110 at one end. The flange is needed to provide an attendant surface for the sanitary cover. Due to the flange 110, the outer cover is often too large to fit under the pen cap 21 (FIGS. 1 and 2). The inner shield 200 is usually small enough such that the inner shield 200 fits under the pen cap 21. In such a case, the outer cover 101 is removed and discarded, and the remaining replacement needle assembly is connected to the drug delivery pen. Thus, both an outer cover and an inner shield must be manufactured to ensure compatibility with existing drug delivery pens, as well as ensuring that the needle is covered while in the assembly.

Drug delivery pens are also disclosed in U.S. Patent Application Publication Nos. 2006/0229562 to Marsh et al. and 2007/0149924 to R. Marsh, the entire contents of both of which are hereby incorporated by reference.

Accordingly, a need exists for an outer cover of a pen needle assembly that is received by a cap of an existing drug delivery pen.

SUMMARY OF THE INVENTION

In accordance with an aspect of the present invention, an outer cover for a pen needle assembly has a breakaway flange that easily separates from the outer cover such that the outer cover may be received by a cap of the pen needle assembly.

In accordance with another aspect of the present invention, a portion of the flange of the outer cover has a reduced cross section to facilitate separation of the flange from the body of the outer cover.

In accordance with another aspect of the present invention, the outer cover has a smaller outer diameter upon separation of the flange such that the outer cover is receivable by an existing pen cap of a pen needle assembly, thereby eliminating the need for a separate inner shield.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying figures, in which.

Throughout the drawings, like reference numbers will be understood to refer to like parts, components and structures.

DETAILED DESCRIPTION OF THE EXEMPLARY EMBODIMENTS

The following description and details of exemplary embodiments of the present invention, while generally disclosed in a typical pen needle assembly, as shown in FIGS. 1 and 2, could more broadly apply to a needle and hub assembly for use in conjunction with, or incorporated onto, other injection devices such as syringes and infusion devices.

In the exemplary embodiments of the present invention shown in FIGS. 5-8, a flange 153 is connected to a body 155 of an outer cover 151 made of a transparent or translucent plastic material. A portion of the flange has a reduced cross sectional thickness, thereby facilitating separation of the flange 153 from the body 155 of the outer cover.

Figure 5:
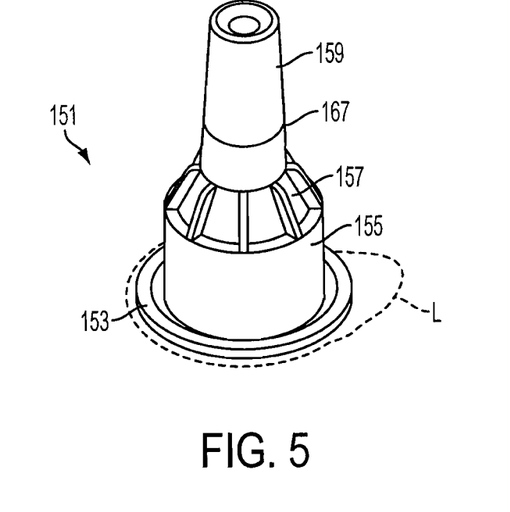
FIG. 5 is a perspective view of a needle cover for a pen needle assembly according to an exemplary embodiment of the present invention.
Figure 6:
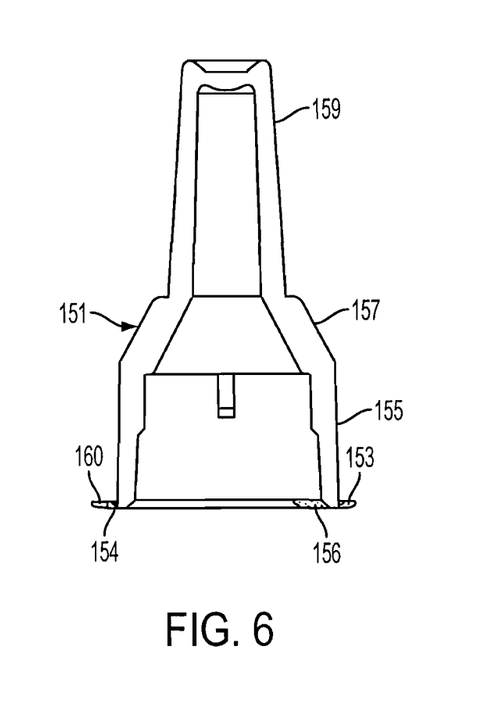
FIG. 6 is an elevational view in cross section of a needle cover according to another exemplary embodiment of the present invention in which a tab is connected to a flange of the needle cover.
Figure 8:
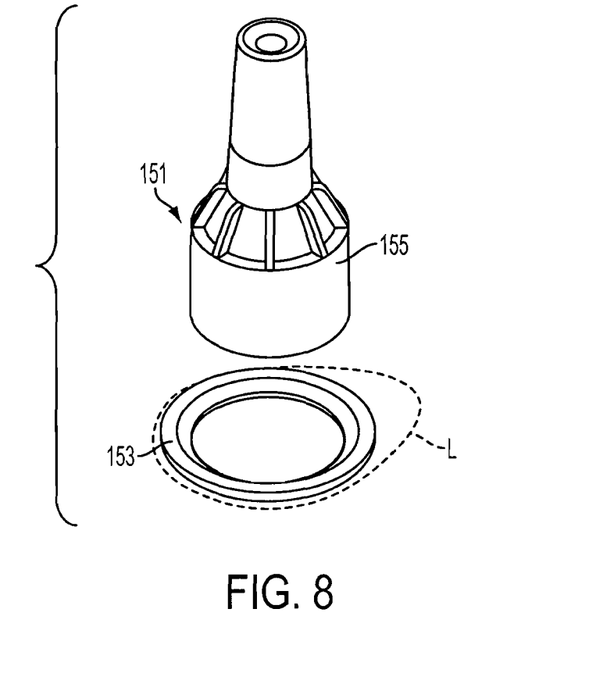
FIG. 8 is a perspective view of the flange separated from the needle cover.

An outer cover 151 has a substantially cylindrical body 155, as shown in FIGS. 5, 6 and 8. A flange 153 is connected to a first end of the body 155. An inwardly tapering body portion 157 is connected to a second end of the body 155. A projection 159 extends outwardly from the tapered body portion 157 in a direction away from the flange 153. The projection 159 is adapted to receive a needle 11 (FIG. 2) of a drug delivery pen 100 (FIGS. 1 and 2).

The flange 153 is substantially circular, as shown in FIGS. 5 and 8. However, the flange may be any shape, such as substantially circular as shown. The flange may also be asymmetric (for example, larger on one side) to allow the user to grasp the flange more easily during removal or to provide asymmetric force distribution to facilitate easy removal.

Figure 7:
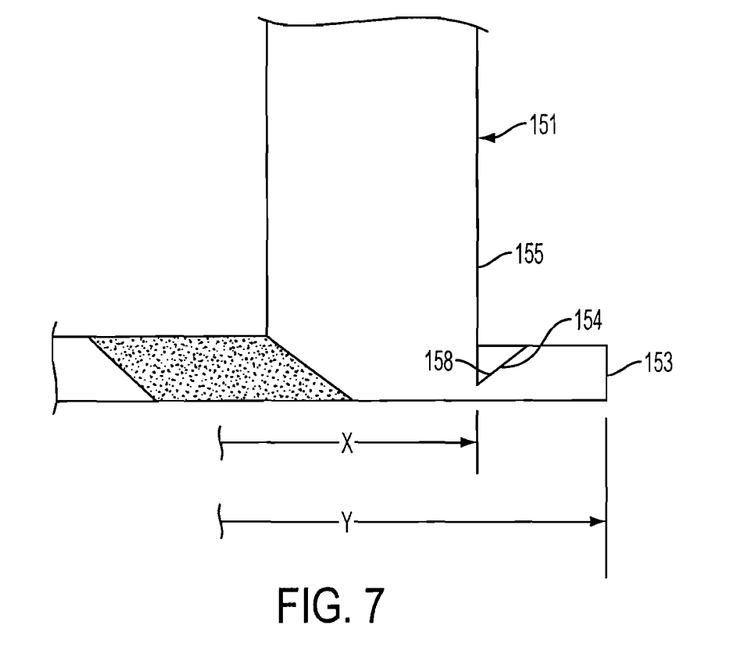
FIG. 7 is an enlarged elevational view of a flange of the needle cover of FIG. 5.

As shown in FIGS. 6 and 7, a portion 154 of the flange 153 has a reduced cross sectional thickness, thereby facilitating separation of the flange from the body 155 of the outer cover 151. As shown in FIG. 6, the reduced cross sectional thickness portion 154 is substantially continuous around the entirety of the flange. However, the reduced cross sectional thickness portion 154 may be of any length that facilitates separation of the flange 153 from the body 155 of the outer cover 151.

Figure 9:
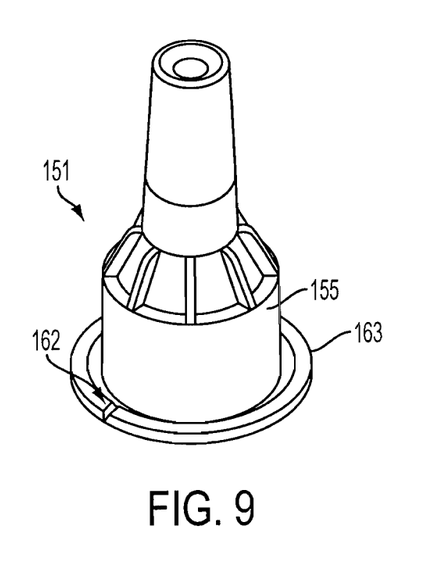
FIG. 9 is a perspective view of a needle cover for a pen needle assembly according to an exemplary embodiment of the present invention.

In this or other embodiments of the present invention, a notch, slit, or cut-out 162 may be present in the flange 163 to provide an easy initiation of the breaking action as shown in FIG. 9. FIG. 9 is a perspective view of a needle cover for a pen needle assembly according to an exemplary embodiment of the present invention. As shown in FIG. 9, the reduced cross-section provides higher stress and initiates the breakage of the flange.

An outer diameter Y of the flange 153 is shown in FIG. 7. This outer diameter generally prevents the outer cover 151 from being received by a pen cap 21 of an existing drug delivery pen 100 (FIGS. 1 and 2). The reduced cross sectional thickness portion 154 of the flange 153 allows the flange to be easily separated from the body 155 of the outer cover 151, thereby reducing the outer diameter to the outer diameter X of the body 155 (i.e., outer diameter X<outer diameter Y). This reduced outer diameter allows the outer cover 151, as shown in FIG. 8, with the flange 153 removed to be received by the pen cap 21 of an existing drug delivery pen 100 (FIGS. 1 and 2).

As shown in FIGS. 5 and 8, a label L (shown in phantom) is attached to a lower surface 156 (FIG. 6) of the flange 153. The label is a sterile barrier for the needle assembly. The lower surface 156 of the flange 153 provides sufficient surface area to which the label is adhered, as well as the flange providing a handle for handling the outer cover during the manufacturing process. The label may also facilitate the removal of the flange 153 as shown in FIG. 8.

As shown in FIGS. 6 and 7, the notch 158 forming the reduced cross sectional thickness portion 154 is substantially triangular. The notch 158 may be any suitable shape, such as triangular, square or circular, that facilitates separation of the flange 153 from the body 155 of the cover 151. By reducing the cross sectional thickness of the flange at a particular location, a small force (pressure) applied to the flange results in an increased stress concentration at the portion of the flange having the reduced cross sectional thickness, thereby resulting in fracture. A tab 160 (FIG. 6) may be connected to the flange 153 to provide a gripping area for separation of the flange from the body 155 of the outer cover 151.

Figure 10:
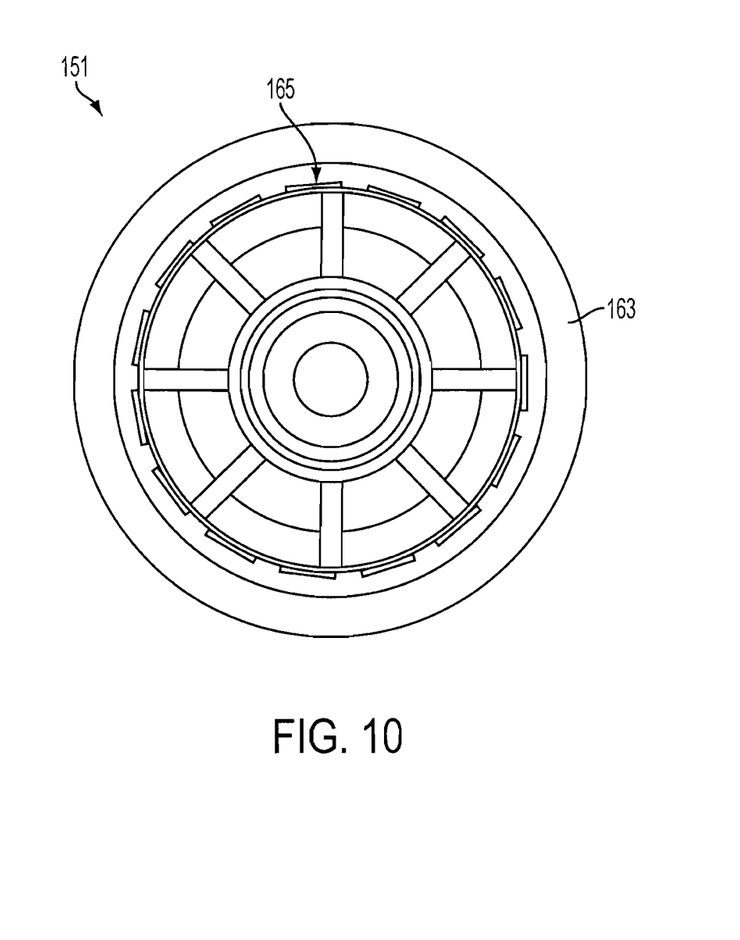
FIG. 10 is a top plan view of a needle cover for a pen needle assembly according to an exemplary embodiment of the present invention.

In this or other embodiments of the present invention, the notch 154 is not required to be continuous around the periphery of the outer cover 151. For example, the notch may be configured as perforations or to contain perforations 165 as shown in FIG. 10. FIG. 10 is a top plan view of a needle cover for a pen needle assembly according to an exemplary embodiment of the present invention. The perforations shown in FIG. 10 reduce the material to be removed while peeling the label and the flange off, thereby resulting in easier removal.

Because the outer cover 151 of the exemplary embodiments of the present invention may be received by a pen cap of an existing drug delivery pen, an inner shield is no longer required to ensure the needle 11 (FIG. 2) is covered. This reduces the number of parts required to be manufactured, thereby reducing costs and lowering inventory.

Figure 11:
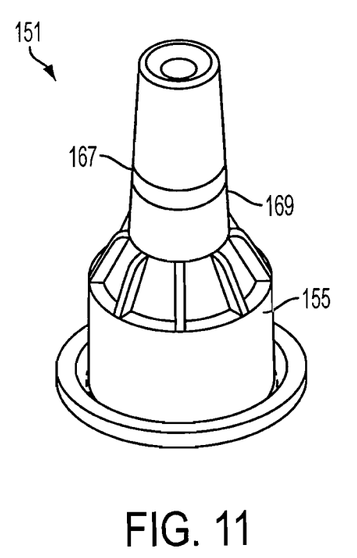
FIG. 11 is a perspective view of a needle cover for a pen needle assembly according to an exemplary embodiment of the present invention.

Returning to FIG. 5, a line 167 on the transparent or translucent outer cover 151 may be used to check a known volume of medication, perform priming and therefore, verify proper dosing. In this or other embodiments of the present invention, a second line 169 may be provided as shown in FIG. 11. FIG. 11 is a perspective view of a needle cover for a pen needle assembly according to an exemplary embodiment of the present invention. In the case of two lines, one line may indicate a maximum volume and the other line may indicate a minimum volume.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention as defined in the appended claims.

What is claimed is:

1. A needle cover for an injection apparatus, comprising: a cap having an open end with an inner dimension for coupling to the injection apparatus; a needle cover having an open first end and a closed second end and having an outer diameter to be received in said open end of said cap; a projection connected to said second end of said cover; a needle received in said cover and said projection; and a breakaway removable flange unitarily formed with said open first end of said cover, a continuous breakable portion between said flange and said cover and surrounding said open first end of said cover, said flange having an outer diameter greater than a diameter of said open end of said needle cover to prevent said open first end of said needle cover from being received in said open end of said cap; a label attached to a bottom face of said flange forming a seal closing said first open end of said cover; wherein when said breakaway flange is attached to said cover, access to an interior of said cover by the injection apparatus is prevented, and when said breakaway flange is removed from said cover to reduce an outer diameter of said cover and to provide an opening to allow access to said interior of said cover by the injection apparatus, said cover and said projection are receivable by said cap of the injection apparatus, said breakaway flange preventing said cover from being received in said open end of the cap prior to removal of said flange.

2. The needle assembly for an injection apparatus according to claim 1, wherein
said removable flange is connected to said first end of said cover and said continuous breakable portion extends around the entirety of said flange.

3. The needle assembly for an injection apparatus according to claim 1, wherein
said removable flange is substantially circular.

4. The needle assembly for an injection apparatus according to claim 1, wherein
said removable flange is asymmetric.

5. The needle assembly for an injection apparatus according to claim 1, wherein
a tab is connected to said removable flange to facilitate removal of said removable flange from said cover.

6. The needle assembly for an injection apparatus according to claim 1, wherein
said continuous breakable portion is defined by a portion of said removable flange having a reduced cross sectional thickness to facilitate removal of said removable flange from said cover.

7. The needle assembly for an injection apparatus according to claim 6, wherein
said reduced cross sectional thickness portion is substantially continuous and extends around an entirety of said removable flange to facilitate removal of said removable flange and label from said cover.

8. The needle assembly for an injection apparatus according to claim 1, wherein
said breakable portion is defined by a notch formed between said removable flange and an outer edge of said cover to facilitate removal of said removable flange from said cover.

9. The needle assembly for an injection apparatus according to claim 1, wherein
said removable flange is perforated to facilitate removal of said removable flange from said cover.

10. The needle assembly for an injection apparatus according to claim 1, wherein
a first circumferential line on said projection facilitates proper dosing.

11. The needle assembly for an injection apparatus according to claim 1, wherein
said projection has first and second circumferential lines to indicate maximum and minimum volumes.

12. The needle assembly claim 1, wherein
said label is attached to a bottom end of said cover and said bottom face of said flange, and where removing said flange from said cover separates said label to access an interior of said cover.

13. A needle assembly for an injection apparatus, comprising: a cap having an open end with an inner dimension for coupling to the injection apparatus; a cover having an open first end and a second end and having an outer dimension to fit within said open end of said cap; a projection connected to said second end of said cover; a needle received in said cover and said projection; and a breakaway removable flange connected to said open first end of said cover, a portion of said breakaway removable flange having a reduced cross sectional thickness extending around said cover to facilitate breaking of said removable flange from said cover, said breakaway flange having an outer dimension preventing said open first end of said cover from fitting into said open end of said cap; wherein when said flange is present on said cover, access to an interior of said cover by the injection apparatus is prevented, and when said flange is removed from said cover to reduce an outer diameter of said cover and to provide an opening in said first end of said cover to allow access to said interior of said cover and coupling to the injection apparatus, and said open first end of said cover and said projection are receivable in said open end of said cap of the injection apparatus, and said flange having an outer dimension greater than said open end of said cap preventing said open first end of said cover from being received in said open end of the cap prior to removal of said flange.

14. The needle assembly for an injection apparatus according to claim 13, wherein said removable flange is substantially circular and has an outer edge spaced radially outward from said cover.

15. The needle assembly for an injection apparatus according to claim 13, wherein
said portion of reduced cross sectional thickness is defined by a notch extending around said cover, and where said removable flange is asymmetric.

16. The needle assembly for an injection apparatus according to claim 13, wherein
said portion of reduced cross sectional thickness is defined by a continuous notch extending around said cover between said cover and said flange, and
a tab is connected to said removable flange to facilitate removal of said removable flange from said cover.

17. The needle assembly for an injection apparatus according to claim 13, wherein
a notch is formed in said removable flange to facilitate removal of said removable flange from said cover.

18. The needle assembly for an injection apparatus according to claim 13, wherein
said removable portion of reduced cross sectional thickness of said removable flange is defined by perforations around said cover to facilitate removal of said removable flange from said cover.

19. The needle assembly for an injection apparatus according to claim 13, wherein
said removable flange has a lower surface facing away from said cover; and
a label is adhered to said lower surface of said removable flange to provide a sterile barrier, wherein removal of said removable flange from said cover removes said label to form an open end of said cover.

20. A method of connecting a needle assembly to an injection apparatus, comprising the steps of: providing a needle assembly including a needle disposed therein, a breakaway removable flange at an open first end of a needle cover of said needle assembly preventing access to an interior of said needle assembly by the injection apparatus, said flange having an outer dimension preventing said first end of said needle cover of said needle assembly from being received in a cap of the injection apparatus, said removable flange having a breakable portion surrounding said needle assembly and having an outer edge spaced outwardly from said needle assembly; breaking and removing the breakaway removable flange from said first end of said cover of said needle assembly to cause an outer diameter of said cover to be less than an inner diameter of an open end of the cap of the injection apparatus and to provide access to said interior of said cover by the injection apparatus, said flange preventing said open first end of said cover from being received in said open end of said cap prior to removal of said flange; connecting the needle assembly to a cartridge of the injection apparatus; and connecting said cap to an outer sleeve of the injection apparatus such that said needle assembly is disposed within said cap.

* * * * *